US006455311B1

(12) United States Patent
Vacanti

(10) Patent No.: US 6,455,311 B1
(45) Date of Patent: Sep. 24, 2002

(54) FABRICATION OF VASCULARIZED TISSUE

(75) Inventor: Joseph P. Vacanti, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/560,480

(22) Filed: Apr. 28, 2000

Related U.S. Application Data

(60) Provisional application No. 60/131,930, filed on Apr. 30, 1999, and provisional application No. 60/165,329, filed on Nov. 12, 1999.

(51) Int. Cl.$^7$ ............................. C12N 5/06; C12N 5/08; A01N 1/00
(52) U.S. Cl. .......................... 435/395; 435/1.1; 435/1.2
(58) Field of Search ............................. 435/1.1–1.3, 395

(56) References Cited

U.S. PATENT DOCUMENTS

| | | | |
|---|---|---|---|
| 5,204,055 A | | 4/1993 | Sachs et al. |
| 5,443,950 A | * | 8/1995 | Naughton et al. |
| 5,686,289 A | | 11/1997 | Humes et al. |

FOREIGN PATENT DOCUMENTS

| | | |
|---|---|---|
| WO | WO 96/09344 A1 | 3/1996 |
| WO | WO 96/40002 A1 | 12/1996 |
| WO | WO 99/52356 A1 | 10/1999 |

OTHER PUBLICATIONS

Marler et al., (Aug. 3 1998) Transplantation of cells in matrices for tissue regeneration, Adv. Drug Delivery Reviews, vol. 33 pp. 165–182.*
Niklason et al., (1997) Advances in tissue engineering of blood vessels and other tissues, Transplant Immunology, vol. 5, pp. 303–306.*
Kim et al. (Jan. 1999) Small intestinal submucosa as a small caliber venous graft, J. Pediatric Surgery, vol. 34, No. 1, pp. 124–128.*
Kim et al (1998) Survival and function of hepatocytes on a novel three–dimensional synthetic biodegradable polymer scaffold with an intrinsic network of channels, Annals of Surgery, vol. 228, No. 1, pp. 8–13.*
Schwerer, et al., "ELISA for determination of albumin in the nanogram range: assay in cerebrospinal fluid and comparison with radial immunodiffusion," *Clin. Chim. Acta.* 163(3):237–44 (1987).
Seglen, "Preparation of isolated rat liver cells," *Methods Cell. Biol.* 13:29–83 (1976).
Sundback & Vacanti, "Alternatives to liver transplantation: From hepatocyte transplantation to tissue–engineered organs," *Gastroenterology* 118:438–442 (2000).
Vacanti & Langer, "Tissue engineering: the design and fabrication of living replacement devices for surgical reconstruction and transplantation," *Lancet* 354 Suppl 1:S132–4 (1999).

Aiken, et al., "Studies in rat liver perfusion for optimal harvest of hepatocytes," *J. Pediatr. Surg.* 25(1):140–5 (1990).
Bell, et al., "Living tissue formed in vitro and accepted as skin–equivalent tissue of full thickness," *Science* 211(4486):1052–4 (1981).
Burke, et al., "Successful use of a physiologically acceptable artificial skin in the treatment of extensive burn injury," *Ann. Surg.* 194(4):413–28 (1981).
Compton, et al., "Skin regenerated from cultured epithelial autografts on full–thickness burn wounds from 6 days to 5 years after grating. A light, electron microscopic and immunohistochemical study," *Lab. Invest.* 60(5):600–12 (1989).
Den Braber, et al., "Orientation of ECM protein deposition, fibroblast cytoskeleton, and attachment complex components on silicone microgrooved surfaces," *J. Biomed. Mater. Res.* 40(2):291–300 (1998).
Despont, et al., "High–Aspect–Ratio, Ultrathick, Negative–Tone Near–UV Photoresist for MEMS", *Proc. of IEEE 10$^{th}$ Annual International Workshop on MEMS*, Nagoya, Japan, pp. 518–522 (Jan. 26–30, 1997).
Folch, et al., "Cellular micropatterns on biocompatible materials," *Biotechnol. Prog.* 14(3):388–92 (1998).
Frazier, et al., "Two dimensional metallic microelectrode arrays for extracellular stimulation and recording of neurons", *IEEE Proceedings of the Micro Electro Mechanical Systems Conference*, pp. 195–200 (1993).
Griffith, et al., "Microfabricated structures for control of 3D cocultures of liver cells," *Annals of Biomed. Eng.*, 26 (1998).
Griffith, et al., "In vitro organogenesis of liver tissue," *Ann. N. Y. Acad. Sci.* 831:382–97 (1997).
Jansen, et al., "The Black Silicon Method IV: The Fabrication of Three–Dimensional Structures in Silicon with High Aspect Ratios for Scanning Probe Microscopy and Other Applications," *IEEE Proceedings of Micro Electro Mechanical Systems Conference*, pp. 88–93 (1995).
Kane, et al., "Patterning proteins and cells using soft lithography," *Biomaterials* 20(23–24):2363–76 (1999).
Laermer, et al., "Bosch Deep Silicon Etching: Improving Uniformity and Etch Rate for Advanced MEMS Applications," *Micro Electro Mechanical Systems*, Orlando, Fl, USA, (Jan. 17–21, 1999).
*Langer & Vacanti, "Tissue engineering," *Science* 260(5110):920–6 (1993).
*Langer & Vacanti, *Sci Am* 280, 62 (1999).

(List continued on next page.)

Primary Examiner—Jon P. Weber
(74) *Attorney, Agent, or Firm*—Thomas J. Kowalski, Esq.; Amy Leahy; Frommer Lawrence & Haug LLP

(57) ABSTRACT

Disclosed and claimed is a laminar structure. The laminar structure has multiple layers. Each layer has tissue and vasculature. The layers are abjacent. The vasculature is in three dimensions through the structure. The structure has connections for flow into and out of the vasculature. The structure can be implanted directly by connecting blood vessels to flow into and out of the vasculature.

7 Claims, 6 Drawing Sheets

OTHER PUBLICATIONS

Lehmann, "Porous Silicon—A New Material for MEMS", *IEEE Proceedings of the Micro Electro Mechanical Systems Conference*, pp. 1–6 (1996).

Lysaght, et al., "An economic survey of the emerging tissue engineering industry," *Tissue Eng.* 4(3):231–8 (1998).

Parenteau, et al., "Biological and physical factors influencing the successful engraftment of a cultured human skin substitute," *Biotechnology and Bioengineering* 52, 3 (1996).

Parenteau, et al., "Epidermis generated in vitro: practical considerations and applications," *J. Cell. Biochem.* 45(3):245–51 (1991).

Peterson, "Effects of the pyrrolizidine alkaloid, lasiocarpine N-oxide, on nuclear and cell division on the liver of rats," *J Pathol Bacteriol* 89, 153 (1965).

Proceedings of the IEEE Micro Electro Mechanical Systems Conference 1987–1998, Rai–Choudbury, ed., *Handbook of Microlithography, Micromachining & Microfabrication* (SPIE Optical Engineering Press, Bellingham, WA 1997).

Purdue, et al., "A multicenter clinical trial of a biosynthetic skin replacement, Dermagraft–TC, compared with cryopreserved human cadaver skin for temporary coverage of excised burn wounds," *J. Burn Care Rehabil.* 18(1 Pt 1):52–7 (1997).

Sachs, et al., "CAD–Casting: Direct Fabrication of Ceramic Shells and Cores by Three Dimensional Printing" *Manufacturing Review* 5(2):117–126 (1992).

* cited by examiner

1. Start Substrate Wafer

2. Deposit Masking Material

3. Pattern Masking Material

4. Etch Substrate Wafer

1. Start Substrate Wafer

2. Deposit Masking Material

3. Pattern Masking Material

4. Etch Substrate Wafer

5. Deposit 2nd Masking Layer

6. Pattern 2nd Masking Layer 7. 2nd Etch Substrate Wafer

8. Remove Masking Layer

FIG. 2A
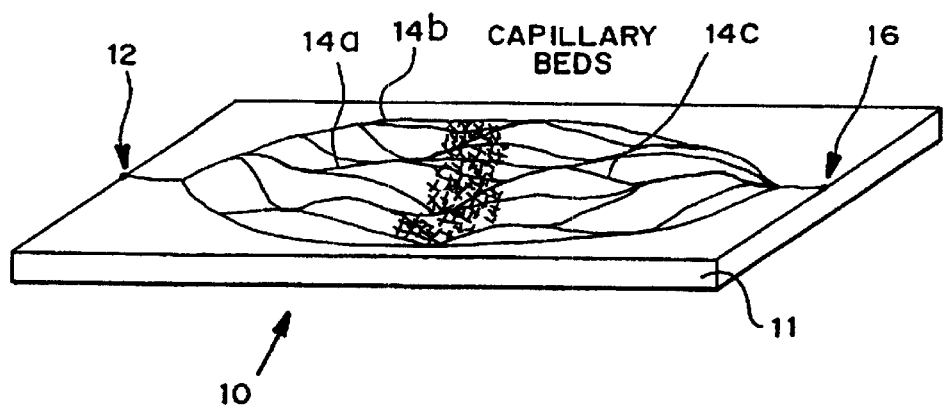
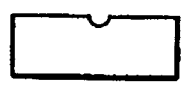
FIG. 2B
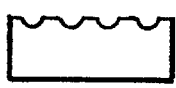
FIG. 2C
FIG. 2D
FIG. 3A  FIG. 3B
 OR  OR
FIG. 3C  FIG. 3D  FIG. 3E
 OR 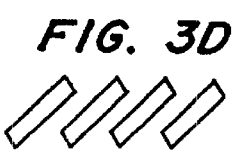 OR 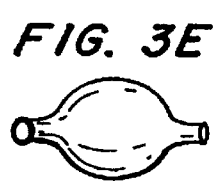
OR 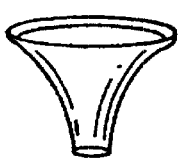 OR 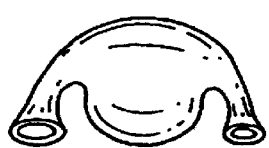
FIG. 3F
FIG. 3G 1. Start Silicon Wafer 2. Pattern Photoresist 3. Isotropic Plasma Etch Silicon 4. Remove Photoresist

FABRICATION OF VASCULARIZED TISSUE

This application claims priority to U.S. Ser. No. 60/131,930 filed Apr. 30, 1999, and U.S. Ser. No. 60/165,329 filed Nov. 12, 1999.

The United States government has certain rights in this invention by virtue of grant number DAMD 17-99-2-9001 from the Department of Defense.

BACKGROUND OF THE INVENTION

The present invention generally relates to the fields of organ transplantation and reconstructive surgery, and to the new field of Tissue Engineering. It more specifically is a new method and materials for generating tissues requiring a blood vessel supply and other complex components such as a nerve supply, drainage system and lymphatic system.

Organ transplantation, as currently practices, has become a major lifesaving therapy for patients afflicted with disease which destroy vital organs including the heart, liver, lungs, kidney and intestine. However, the shortage of organs needed for transplantation has become critical and continues to worsen. Likewise, every major field of reconstructive surgery reaches the same barrier of tissue shortage. Orthopedic surgery, vascular surgery, cardiac surgery, general surgery, neurosurgery, and the others all share this fundamental problem. Therefore, countless patients suffer as a result.

Over the last twelve years, the new field of tissue engineering has arisen to meet this need. The field brings the expertise of physicians, life scientists and engineers together to solve problems of generating new tissues for transplantation and surgical reconstruction. The initial approaches to this problem were described in the 1980's. Yannas and Burke (Bell, et al., *Science* 221,1052 (1981); Burke, et al., *Ann Surg* 194, 413 (1981)( described methods to generate new tissues in vivo by implanting non-living materials such as modified collagens which are seeded with cells to promote guided regeneration of tissue such as skin. Vacanti and Langer (Langer and Vacanti *Science* 260, 920 (1993); Vacanti, et al., Materials Research Society 252,367 (1992)) described synthetic fibrous matrices to which tissue specific cells were added in vitro. The matrices are highly porous and allow mass transfer to the cells in vitro and after implantation in vivo. After implantation, new blood vessels grow into the devices to generate a new vascularized tissue. However, the relatively long time course for angiogenesis limits the size of the newly formed tissue.

The field of Tissue Engineering is now maturing and undergoing explosive growth. See, for example, Vacanti and Langer, *Lancet* 354, 32 (1999); Langer and Vacanti *Science* 260, 920 (1993); Rennie, J. ed. Special report: The promise of tissue engineering. *Scientific American* 280, 37 (1999); and Lysaght, et al., *Tissue Eng* 4, 231 (1998). Virtually every tissue and organ of the body has been studied. Many tissue-engineering technologies are becoming available for human use. See, Lysaght, et al. *Tissue Eng* 4, 231 (1998); Bell, et al., *Science* 221,1052 (1981); Burke, et al.,*Ann Surg* 194, 413 (1981); Compton, et al., *Laboratory Investigation* 60, 600 (1989); Parenteau, et al., *Journal of Cellular Biochemistry* 45, 24 (1991); Parenteau, et al., *Biotechnology and Bioengineering* 52, 3 (1996); Purdue, et al., *J. Burn Care Rehab* 18, 52 (1997); Hansbrough and Franco, *Clinical Plastic Surg* 25, 407 (1998); Vacanti, et al., Materials Research Society 252,367 (1992).

Over time, several techniques to engineer new living tissue have been studied. Technologies include the use of growth factors to stimulate wound repair and regeneration, techniques of guided tissue regeneration using non-living matrices to guide new tissue development, cell transplantation, and cell transplantation on matrices. More recently, new understanding in stem cell biology has led to studies of populations of primordial cells, stem cells, or embryonic stem cells to use in tissue engineering approaches.

To date, all approaches in tissue engineering have relied on the in-growth of blood vessels into tissue-engineered devices to achieve permanent vascularization. This strategy has worked well for many tissues. However, it falls short for thick, complex tissues such as large vital organs, including liver, kidney, and heart. Techniques using three-dimensional printing technology to achieve ordered arrays of channels have been described to begin to solve this problem. See, for example, Griffith, et al., *Ann NY Acad Sci* 831, 382 (1997); Langer and Vacanti JP *Sci Am* 280, 62 (1999).

In parallel to these advances, the rapidly emerging field of MicroElectroMechanical Systems (MEMS) has penetrated a wide array of applications, in areas as diverse as automotives, inertial guidance and navigation, microoptics, chemical and biological sensing, and, most recently, biomedical engineering, Langer and Vacanti *Sci Am* 280, 62 (1999); McWhorter, et al. "Micromachining and Trends for the Twenty-First Century", in *Handbook of Microlithography, Micromachining and Microfabrication*, ed. P. Rai-Choudhury, (Bellingham, Wash: SPIE Press, 1997). Microfabrication methods for MEMS represent an extension of semiconductor wafer process technology originally developed for the integrated circuit (IC) industry. Control of features down to the submicron level is routinely achieved in IC processing of electrical circuit elements; MEMS technology translates this level of control into mechanical structures at length scales stretching from less than 1 micron to greater than 1 cm. Standard bulk micromachining enables patterns of arbitrary geometry to be imprinted into wafers using a series of subtractive etching methods. Three-dimensional structures can be realized by superposition of these process steps using precise alignment techniques. Several groups (Kourepenis, et al., "Performance of MEMS Inertial Sensors," Proc. AIAA GN&C Conference, Boston, Mass., 1998; Griffith, et al., *Annals of Biomed Eng.*, 26 (1998); Folch, et al., *Biotechnology Progress*, 14, 388 (1998)) have used these highly precise silicon arrays to control cell behavior and study gene expression and cell surface interactions. However, this approach is essentially a two-dimensional technology and it has not been apparent that it might be adapted to the generation of thick, three-dimensional tissues.

PCT US96/09344 by Massachusetts Institute of Technology describe a three-dimensional printing process, a form of solid free form fabrication, which builds three-dimensional objects as a series of layers. This process uses polymer powders in layers bound by polymer binders whose geometry is dictated by computer assisted design and manufacture. This technique allows defined internal architectures which could include branching arrays of channels mimicking a vascular supply. However, this technique is limited by the characteristics and chemistry of the particular polymers. Also, it severely limits the types of tissue to be fabricated. Polymer walls do not allow the plasma exchange that is needed at the alveolar capillary wall of the lung.

The object of the present invention is to provide a method and materials for creating complex, living vascularized tissues for organ and tissue replacement, especially complex and/or thick structures, such as liver tissue.

SUMMARY OF THE INVENTION

A method and materials to create complex vascularized living tissue in three dimensions from a two-dimension microfabricated mold has been developed. The method involved creating a two dimensional surface having a branching structure etched into the surface. The pattern begins with one or more large channels which serially branch into a large array of channels as small as individual capillaries, then converge to one or more large channels. The etched surface serves a template within a mold formed with the etched surface for the circulation of an individual tissue or organ. Living vascular cells are then seeded onto the mold, where they form living vascular channels based on the pattern etched in the mold. Once formed and sustained by their own matrix, the top of the mold is removed. The organ or tissue specific cells are then added to the etched surface, where they attach and proliferate to form a thin, vascularized sheet of tissue. The tissue can then be gently lifted from the mold using techniques such as fluid flow and other supporting material, as necessary. The tissue can then be systematically folded and compacted into a three-dimensional vascularized structure. This structure can then be implanted into animals or paitents by directly connecting the blood vessels to flow into and out of the device. Immediate perfusion of oxygenated blood occurs, which allows survival and function of the entire living mass.

The design of the branching channels can be constructed by a number of means, such as fractal mathematics which can be converted by computers into two-dimensional arrays of branches and then etched onto wafers. Also, computers can model from live or preserved organ or tissue specimens three dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques. The two-dimensional surface of the mold can also be varied to aid in the folding and compacting process. For example, the surface can be changed from planar to folded accordian like. It can be stacked into multiple coverging plates. It could be curvilinear or have multiple projections.

Different types of tissue, or multiple layers of the same type of tissue, can be placed adjacent to each other prior to folding and compacting, to create more complex or larger structures. For example, a tubular system can be layered onto a vascular system to fabricate glomerular tissue and collecting tubules for kidneys. Bile duct tubes can be onlaid over vascularized liver or hepatocyte tissue, to generate a bile duct drainage system. Alveolar or airway tissue can be placed on lung capillaries to make new lung tissue. Nerves or lymphatics can be added using variations of these same general techniques. The two-dimensional surface of the mold can also be varied to aid in the folding and compacting process. For example, the surface can be changed from planar to folded accordian like. It can be stacked into multiple coverging plates. It could be curvilinear or have multiple projections.

Examples of tissues and organs which can be fabricated using these methods include, but are not restricted to, organs currently transplanted such as heart, liver, lung, kidney and intestine. Other tissues such as muscle, bone and breast tissue could also be engineered.

BRIEF DESCRIPTION OF THE DRAWINGS

FIG. 2a is a schematic of an etched surface showing a branching structure which branches out from a single inlet and then converges back into a single outlet. FIGS. 2b, c, and d are schematics of a cross-sectional view of different etched channels in the surface of FIG. 2a.

FIGS. 3a–g are schematics of multiple tissue layers assembled to form three dimensional structures.

DETAILED DESCRIPTION OF THE INVENTION

Figure 1A:
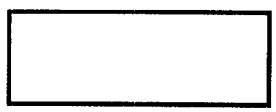
FIG. 1a is a schematic of the process for making a branching pattern ono a silicon substrate.
Figure 1A:
Figure 1A:
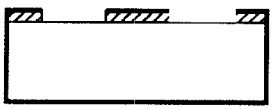
Figure 1A:
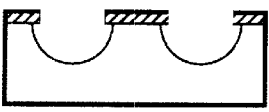

Due to the difficulties of the prior art, an approach to provide a complete vascular system to the engineered structure before implantation was developed using microfabrication techniques such as three dimensional printing to provide an ordered array of branching channels in a substrate formed of a material such as silicon or a biocompatible polymer, which are then seeded with cells. A complete branching vascular circulation is made in two dimensions on the surface of silicon using microfabrication. The vascular circulation is then lifted from the silicon mold and folded or rolled into a compact three dimensional structure.

Microfabrication technology has been used in important studies in cell and developmental biology to understand complex biologic signaling events occurring at the cell membrane-surface interface, as described, for example, by Kane, et al., *Biomaterials* 20, 2363 (1999). It has also been used in tissue engineering to guide cell behavior and the formation of small units of tissue, as described by Griffith, et al., *Annals of Biomed. Eng.,* 26 (1998). As demonstrated by Example 1, a coherent structure over a broad range of scale has now been made which demonstrates the efficacy of this method for tissue engineering for construction of complex and/or thick structures such as liver. The device constructed in the example includes channels that begin as a single inlet channel with a diameter of 500 microns, branch through four generations following a geometric scaling law which halves the channel width for each successive generation, form an array of capillary channels 10 microns in diameter, and then sequentially branch back to a single outflow vein. Living endothelial cells seeded into these channels and provided with flow of appropriate nutrients and gases will line the channels to form blood vessels. In Example 2, it has been demonstrated that cells seeded onto surfaces of silicon and pyrex will lay down matrix and form sheets of tissue of the cell type of origin, either hepatic or endothelial. These sheets can be peeled from the surface and formed into three dimensional units of tissue. In effect, the wafer of silicon or pyrex has acted as a mold for the formation of tissue.

These examples demonstrate that microfabrication technology can be adapted to suit the needs of forming living tissue. The power of the technique lies in its control of form over extremely small distances. The resolution is on the order of 0.1 microns from point to point. This level of precision adds new levels of control in the ability to design and guide new tissue formation. For instance, surfaces can be imprinted with submicron grooves or scallops, and corners can be made rounded, angled or sharp with this same level of submicron precision. Geometric control at this scale can have a powerful impact on cell adhesion through mechanisms such as contact guidance, as described by Den Braber, et al. *J. Biomed. Mater. Res.* 40, 291 (1998). This technology overcomes the problems with the prior art which was limited to very thin structures because designs were constrained to the surface of the silicon wafers. Using the wafer as a temporary mold, then lifting the tissue from it and folding the tissue into three-dimensional space, overcomes this limitation.

As described herein, complex tissues are formed by laminating layers of thin vascularized tissues to form thicker tissue structures or more complex organ equivalents. The thin vascularized tissue layers are formed by:

(1) designing a mold having a complex pattern of channels formed into at least one surface into which cells can be seeded;

(2) seeding vascular (endothelial) cells into the channels;

(3) culturing the vascular cells under conditions until they form vasculature;

(4) seeding other type(s) of cells onto or into the mold so that a tissue is formed incorporating the vasculature;

(5) removing the vascularized tissue layer; and (6) assembling multiple layers of the vascularized tissue layers until the desired complex structure (or organ equivalent) is formed.

This structure can then be implanted and the vasculature, if properly designed, anastomized into the existing vasculature to provide an immediate blood supply for the implanted organ equivalent.

Molds for Manufacturing Thin Vascularized Tissue Layers

Materials for Forming Molds

Fabrication of the wafer molds begins by selection of an appropriate substrate. Any of a variety of materials can be used to form the surfaces on which the branching structures can be molded or etched. These include "inert" materials such as silicone, polymers such as polyethylene vinyl acetate, polycarbonate, and polypropylene, and materials such as a ceramic or material such as hydroxyapatite. In particular, the mold can be constructed from metals, ceramics, semiconductors, organics, polymers, and composites. Representative metals and semiconductors include pharmaceutical grade stainless steel, gold, titanium, nickel, iron, gold, tin, chromium, copper, alloys of these or other metals, silicon, silicon dioxide.

Typically, micromachining is performed on standard bulk single crystal silicon wafers of a diameter ranging between 50 and 300 millimeters, and of thickness ranging between 200 and 1200 microns. These wafers can be obtained from a large number of vendors of standard semiconductors material, and are sawn and polished to provide precise dimensions, uniform crystallographic orientation, and highly polished, optically flat surfaces. Wafers made from pyrex borosilicate or other glasses can also be procured and inserted into micromachining processes, with alternative processes used to etch the glassy materials.

The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Cost may also be a consideration, depending upon the overall size requirements of the tissue mold.

Unless otherwise specified, the term "polymer" includes polymers and monomers which can be polymerized or adhered to form an integral unit. The polymer can be non-biodegradable or biodegradable, typically via hydrolysis or enzymatic cleavage, although biodegradable matrices are not typically preferred since the molds are not implanted and are preferably reusable. Non-polymeric materials which can also be used include organic and inorganic materials such as hydoxyapatite, calcium carbonate, which are solidified by application of adhesive rather than solvent. In a preferred embodiment, polymers are selected based on the ability of the polymer to elicit the appropriate biological response from cells, for example, attachment, migration, proliferation and gene expression. As noted above, many non-biodegradable plastics are known which are currently in use in cell culture, including polystyrene, polycarbonate, polypropylene, polyvinylacetate, as well as biodegradable polymers such as polyhydroxy acids and polyhydroxyalkanoates. Photopolymerizable, biocompatible water-soluble polymers include polyethylene glycol tetraacrylate (Ms 18,500) which can be photopolymerized with an argon laser under biologically compatible conditions using an initiator such as triethanolamine, N-vinylpyrrolidone, and eosin Y. Other suitable polymers can be obtained by reference to The Polymer Handbook, 3rd edition (Wiley, N.Y., 1989).

Solvents for most of the thermoplastic polymers are known, for example, methylene chloride or other organic solvents. Organic and aqueous solvents for protein and polysaccharide polymers are also known. The binder can be the same material as is used in conventional powder processing methods or may be designed to ultimately yield the same binder through chemical or physical changes that occur as a result of heating, photopolymerization, or catalysis.

These can be coated with a material enhancing cell adhesion. In some embodiments, attachment of the cells to the polymer is enhanced by coating the substrate with compounds such as basement membrane components, agar, agarose, gelatin, gum arabic, collagens types I, II, III, IV, and V, fibronectin, laminin, glycosaminoglycans, mixtures thereof, and other materials known to those skilled in the art of cell culture.

Properties of the mold surface can also be manipulated through the inclusion of materials on or in the mold material which alters porosity, cell attachment (for example, by altering the surface charge or structure), flexibility or rgidity (which may be desirable to facilitate removal of tissue constructs).

Methods for Designing Mold Surfaces

Once the substrate material has been selected, the process sequence for mold generation must be defined. The geometry of the mold, in particular the number of different feature depths required, is the major factor determining the specific process sequence. The simplest case is that of a single depth dimension for the mold. Specifically, for a silicon substrate, the process sequence (shown in FIG. 1a) is as follows: First, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semi-transparent mask. This step can be accomplished using any one of several masking techniques, depending on the desired image resolution. The resist is then developed in an appropriate developer chemistry, and the wafer is then hard-baked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding process.

Glass and polymeric wafer molds can be fabricated using a similar sequence, but the actual process may be modified by the addition of an intervening masking layer, since etchants for these materials may attack photoresist as well. Such intervening materials simply function to transfer the pattern from the photoresist to interlayer and then on to the wafer below. For silicon etched in one of several wet chemistries, an intervening layer may also be necessary.

Figure 1B:
FIG. 1b is a more detaild schematic showing the process to make a more complex structure, with channels of varying depths.
Figure 1B:
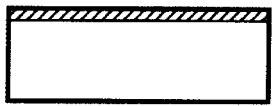
Figure 1B:
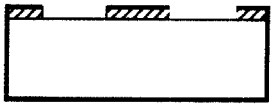
Figure 1B:
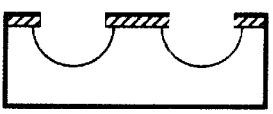
Figure 1B:
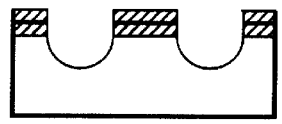
Figure 1B:
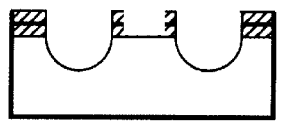
Figure 1B:
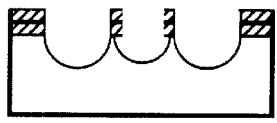
Figure 1B:
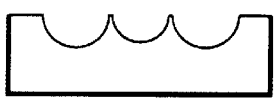

Increased flexibility in the geometry of wafer mold may be obtained by inserting additional cycles of masking and etching, as shown in FIG. 1b. Here, a second step in which a masking layer has been applied and open areas etched is shown. This modification provides the opportunity to machine channels of varying depths into the wafer mold. For vascular branches with different diameters, this increased flexibility becomes very important. The techniques may be extended to provide as many additional layers and different depths as is desired.

The mold surface is configured as required to create tissue sections having the desired vascular or other tubular structures. In the case where a naturally occurring structure is mimicked, channels are etched in the same two-dimensional pattern that occurs in the natural tissue. A difference is that the natural tissue will not be limited to a two-dimensional structure, but instead would include vasculature that extends three dimensionally. This differs from the thin tissue or organ sections created as described herein.

The design of the branching channels can be constructed by a number of means, such as fractal mathematics which can be converted by computers into two-dimensional arrays of branches and then etched onto wafers. Also, computers can model from live or preserved organ or tissue specimensthree dimensional vascular channels, convert to two-dimensional patterns and then help in the reconversion to a three-dimensional living vascularized structure. CAD-CAM type software programs would typically be most useful for design of these structures.

Methods for Configuring the Molds

The selection of the material which is used as the support determines how the surface of the mold is configured to form the branching structure. Materials can be configured by molding, particularly in the case of polymers, etching using techniques such as lasers, plasma etching, or chemical etching, photolithography, or solid free form techniques including three dimensional printing (3DP), stereolithography (SLA), selective laser sintering (SLS), ballistic particle manufacturing (BPM) and fusion deposition modeling (FDM), micromachining, or combinations thereof.

Conventional Polymer Processing

Polymers can be configured using standard techniques such as solvent casting or extrusion molding into a prefabricated mold, shaped using one of the solid free form techniques or configured after shaping, using chemical etching, micromachining, lasers, or other methods described herein. These methods can also be used to form the molds from materials other than polymers.

Micromachining and Chemical Processing of Silicon Materials

In one embodiment, the mold devices are made by microfabrication processes, by creating small mechanical structures in silicon, metal, polymer, and other materials. These microfabrication processes are based on well-established methods used to make integrated circuits and other microelectronic devices, augmented by additional methods developed by workers in the field of micromachining.

Microfabrication processes that may be used in making the molds disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); *Proceedings of the IEEE Micro Electro Mechanical Systems Conference* 1987–1998; Rai-Choudhury, ed., *Handbook of Microlithography Micromachining & Microfabrication* (SPIE Optical Engineering Press, Bellingham, Wash. 1997). The following methods are preferred for making molds.

Electrolytic anodization of silicon in aqueous hydrofluoric acid, potentially in combination with light, can be used to etch channels into the silicon. By varying the doping concentration of the silicon wafer to be etched, the electrolytic potential during etching, the incident light intensity, and the electrolyte concentration, control over the ultimate pore structure can be achieved.

This process uses deep plasma etching of silicon to create molds with diameters on the order of 0.1 $\mu$m or larger. Needles are patterned directly using photolithography, rather than indirectly by controlling the voltage (as in electrochemical etching), thus providing greater control over the final mold geometry.

In this process, an appropriate masking material (e.g., metal) is deposited onto a silicon wafer substrate and patterned into dots having the diameter of the desired molds. The wafer is then subjected to a carefully controlled plasma based on fluorine/oxygen chemistries to etch very deep, high aspect ratio trenches into the silicon. See, e.g., Jansen, et al., "The Black Silicon Method IV: The Fabrication of Three-Dimensional Structures in Silicon with High Aspect Ratios for Scanning Probe Microscopy and Other Applications," *IEEE Proceedings of Micro Electro Mechanical Systems Conference*, pp. 88–93 (1995).

In this process, a metal layer is first evaporated onto a planar substrate. A layer of photoresist is then deposited onto the metal to form a patterned mold which leaves an exposed-metal region in the shape of needles. By electroplating onto the exposed regions of the metal seed layer, the mold bounded by photoresist can be filled with electroplated material. Finally, the substrate and photoresist mold are removed, leaving the finished mold array. The molds produced by this process generally have diameters on the order of 1 μm or larger. See, e.g., Frazier, et al., "Two dimensional metallic microelectrode arrays for extracellular stimulation and recording of neurons", *IEEE Proceedings of the Micro Electro Mechanical Systems Conference*, pp. 195–200 (1993).

Another method for forming molds made of silicon or other materials is to use microfabrication techniques to make a mold form, transferring that mold form to other materials using standard mold transfer techniques, such as embossing or injection molding, and reproducing the shape of the original mold form using the newly-created mold to yield the final molds. Alternatively, the creation of the mold form could be skipped and the mold could be microfabricated directly, which could then be used to create the final molds.

Another method of forming solid silicon molds is by using epitaxial growth on silicon substrates, as is utilized by Containerless Research, Inc. (Evanston, Ill., USA) for its products.

The size distribution of the etched porous structure is highly dependent on several variables, including doping kind and illumination conditions, as detailed in Lehmann, "Porous Silicon—A New Material for MEMS", *IEEE Proceedings of the Micro Electro Mechanical Systems Conference*, pp. 1–6 (1996). Porous polymer molds can be formed, for example, by micromolding a polymer containing a volatilizable or leachable material, such as a volatile salt, dispersed in the polymer, and then volatilizing or leaching the dispersed material, leaving a porous polymer matrix in the shape of the mold. Hollow molds can be fabricated, for example, using combinations of dry etching processes (Laermer, et al., "Bosch Deep Silicon Etching: Improving Uniformity and Etch Rate for Advanced MEMS Applications," *Micro Electro Mechanical Systems*, Orlando, Fla., USA, (Jan. 17–21, 1999); Despont et al., "High-Aspect-Ratio, Ultrathick, Negative-Tone Near-UV Photoresist for MEMS", *Proc. of IEEE 10$^{th}$ Annual International Workshop on MEMS*, Nagoya, Japan, pp. 518–522 (Jan. 26–30, 1997)); micromold creation in lithographically-defined polymers and selective sidewall electroplating; or direct micromolding techniques using epoxy mold transfers.

A chromium mask can be substituted for the solid molds using a silicon nitride layer covered with chromium. Solid molds are then etched, the chromium is stripped, and the silicon is oxidized. The silicon nitride layer will prevent oxidation. The silicon nitride is then stripped, leaving exposed silicon and oxide-covered silicon everywhere else. The needle is then exposed to an ICP plasma which selectively etches the silicon in a highly anisotropic manner to form the interior hole of the needle. A second method uses solid silicon as 'forms' around which the actual needle structures are deposited. After deposition, the forms are etched away, yielding the hollow structures. Silica needles or metal needles can be formed using different methods. The wafers are then oxidized to a controlled thickness, the silicon nitride is then stripped and the silicon core selectively etched away (e.g., in a wet alkaline solution) to form a hollow silica mold.

In another embodiment, deep reactive ion etching is combined with a modified black silicon process in a conventional reactive ion etcher. First, designs are patterned through photoresist into $SiO_2$, such as on a silicon wafer. Then the silicon can be etched using deep reactive ion etching (DRIE) in an inductively coupled plasma (ICP) reactor to etch deep vertical holes or channels. The photoresist is then removed. Next, a second photolithography step patterns the remaining $SiO_2$ layer. The photoresist is then removed and the silicon wafer again deep silicon etched completely through the wafer in the regions not covered with $SiO_2$). This process can be varied as follows. After the wafer is patterned, the photoresist and $SiO_2$ layers are replaced with conformal DC sputtered chromium. The second ICP etch is replaced with a $SF_6/O_2$ plasma etch in a reactive ion etcher (RIE), which results in positively sloping outer sidewalls. Henry, et al., "Micromachined Needles for the Transdermal Delivery of Drugs," *Micro Electro Mechanical Systems*, Heidelberg, Germany, pp. 494–498 (Jan. 26–29, 1998).

Metal shapes can be formed by physical vapor deposition of appropriate metal layers on solid forms, which can be made of silicon using the techniques described above, or which can be formed using other standard mold techniques such as embossing or injection molding. The metals are selectively removed using electropolishing techniques, in which an applied anodic potential in an electrolytic solution will cause dissolution of metals due to concentration of electric field lines. Once the underlying silicon forms have been exposed, the silicon is selectively etched away to form structures. This process could also be used to make structures made from other materials by depositing a material other than metal on the needle forms and following the procedure described above.

Molds formed of silicon dioxide can be made by oxidizing the surface of the silicon mold forms, rather than depositing a metal and then etching away the solid needle forms to leave the hollow silicon dioxide structures. In one embodiment, hollow, porous, or solid molds are provided with longitudinal grooves or other modifications to the exterior surface of the molds.

Polymeric molds can be made using microfabricated molds. For example, the epoxy molds can be made as described above and injection molding techniques can be applied to form the structures. These micromicromolding techniques are relatively less expensive to replicate than the other methods described herein.

Solid Free Form Methods for Configuring the Molds

3DP is described by Sachs, et al., "CAD-Casting: Direct Fabrication of Ceramic Shells and Cores by Three Dimensional Printing" *Manufacturing Review* 5(2), 117–126 (1992) and U.S. Pat. No. 5,204,055 to Sachs, et al. 3DP is used to create a solid object by ink-jet printing a binder into selected areas of sequentially deposited layers of powder. Each layer is created by spreading a thin layer of powder over the surface of a powder bed. The powder bed is supported by a piston which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

SFF methods other than 3DP that can be utilized to some degree as described herein are stereo-lithography (SLA), selective laser sintering (SLS), ballistic particle manufacturing (BPM), and fusion deposition modeling (FDM). SLA is based on the use of a focused ultra-violet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials. SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y. FDM employs an x-y plotter with a z motion to position an extrudable filament formed of a polymeric material, rendered fluid by heat or the presence of a solvent. A suitable system is available from Stratasys, Incorporated of Minneapolis, Minn.

Cells for Forming Vascularized Tissue Layers

Although described herein with particular reference to formation of vascularized tissue, it should be understood that the channels can be used for form lumens for passage of a variety of different fluids, not just blood, but also bile, lymph, urine, and other body fluids, and for the guided regeneration or growth of other types of cells, especially nerve cells. The tissue layer may include some lumens for forming vasculature and some for other purposes, or be for one purpose, typically providing a blood supply to carry oxygen and nutrients to and from the cells in the tissue.

The tissue will typically include one or more types of "functional" or parenchymal cells, such as cells having specific metabolic functions, like hepatocytes, pancreatic cells, kidney, brain, reproductive tissue cells, cells forming intestine, nerve cells, bone, muscle, heart, skin cells, etc. The vasculature will typically be formed from endothelial cells.

Cells can be obtained by biopsy or harvest from a living donor, cell culture, or autopsy. Cells can be dissociated using standard techniques such as digestion with collagenase, then seeded immediately into the mold or after being maintained in cell culture. Cells can be normal cells or genetically engineered, from the patient into which the tissue is to be implanted, or from a suitable donor.

Methods for Seeding Cells into Molds

A method and materials to create complex vascularized living tissue in three dimensions from a two-dimension microfabricated mold has been developed. The method involved creating a two dimensional surface having a branching structure etched into the surface. As shown in FIG. 2a, in a preferred embodiment, the pattern in the mold 10 formed of a silicon wafer 11 begins with one or more large channels 12 which serially branch into a large array of channels as small as individual capillaries 14a, 14b, 14c, etc., then converge to one or more large channels 16. The cross section of the single "arterial" channel 12 and "venous" channel 16 are shown in FIG. 2b. The cross-sections of the portion of mold 10 containing the "capillary" channels 14a, 14b, 14c, etc., is shown in FIG. 2c. The mold is shown in cross-section in FIG. 2d, with a depth of approximately five microns.

Figure 4A:
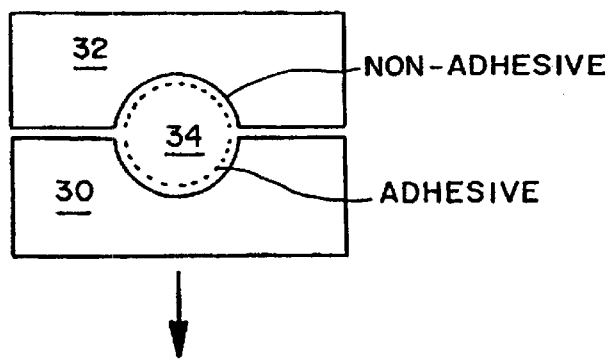
FIGS. 4a, b and c are schematics of the process for making a tissue layer.
Figure 4B:
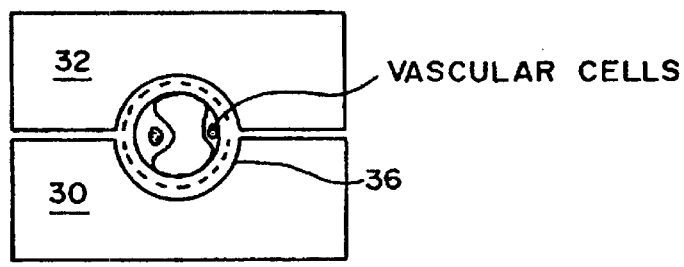
Figure 4C:
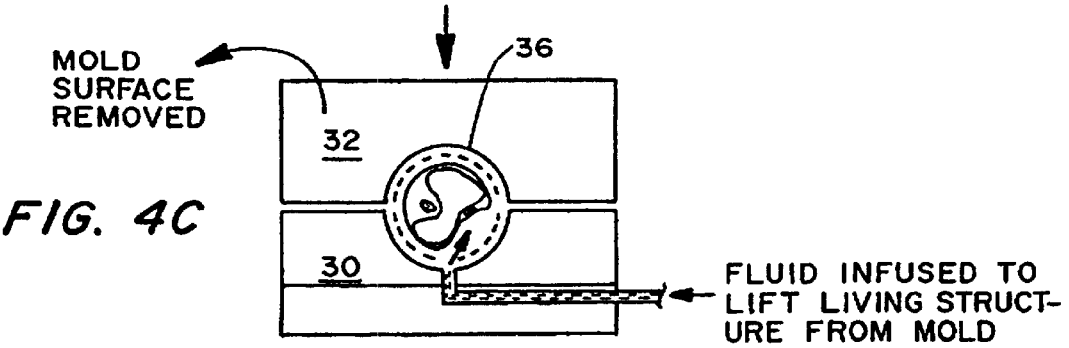

The etched surface serves as a template within a mold formed with the etched surface for the circulation of an individual tissue or organ. As shown in FIG. 4A, the mold pieces 30 and 32 are fitted together to make an enclosure 34, and the cells cultured. The vascular cells form vascular channels 36 based on the pattern etched in the mold, as shown in FIG. 4B. Once formed and sustained by their own matrix, the top 32 of the mold is removed, and the organ or tissue specific cells are then added to the etched surface, where they attach and proliferate to form a thin, vascularized sheet of tissue 36. As shown in FIG. 4C, the tissue can then be gently lifted from the mold using techniques such as fluid flow and other supporting material, as necessary.

Construction of Tissue or Organ Equivalents

Figure 5:
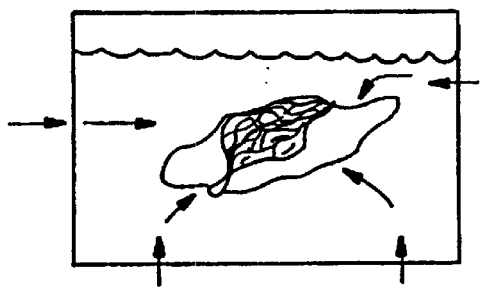
FIG. 5 is a schematic of an assembled complex tissue or organ formed by the process of FIGS. 4a–c.

After formation of the tissue layers, the tissue can be systematically folded and compacted into a three-dimensional vascularized structure, as shown in FIG. 5. The two-dimensional surface of the mold can be varied to aid in the folding and compacting process. For example, the surface can be changed from planar to folded accordian like. It can be stacked into multiple coverging plates. It could be curvilinear or have multiple projections.

FIGS. 3A–G are perspective views of ways in which a single tissue layer 36 (FIG. 3A) can be folded (FIGS. 3B and 3C) or stacked (FIG. 3D), or expanded to form a balloon shape (FIG. 3E), funnel (FIG. 3F), or large lumen (FIG. 3G).

Figure 6:
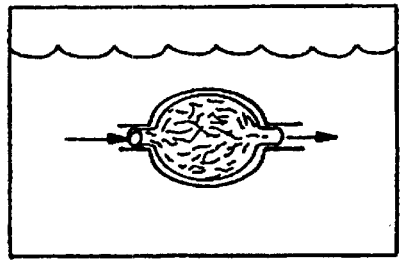
FIG. 6 shows how the organ of FIG. 5 can be connected to a fluid by anastomosis of the inlet and outlet.
Figure 7:
FIG. 7 is a schematic of the pattern etched using an inductively-coupled (IPC) system.
Figure 7:
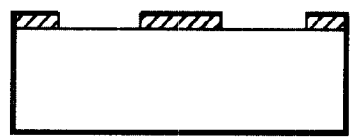
Figure 7:
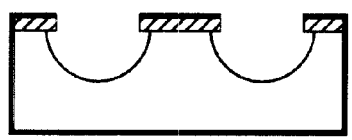
Figure 7:
Figure 8:
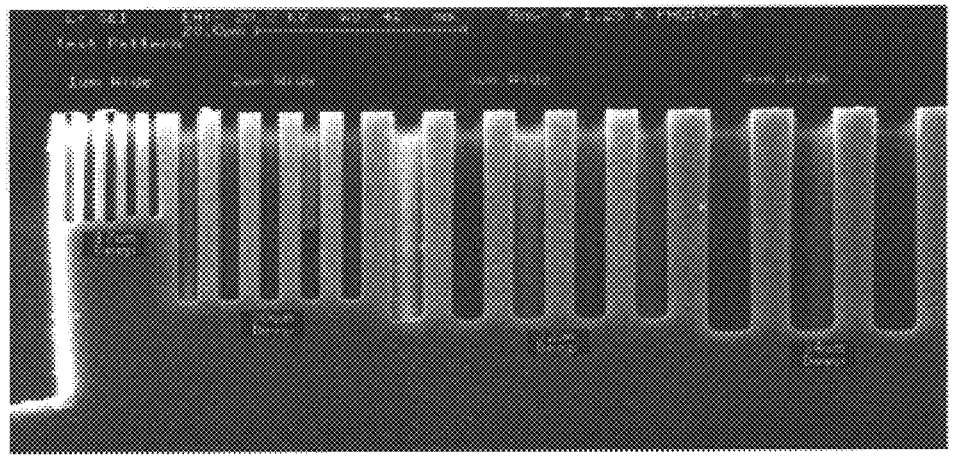
FIG. 8 is a schematic of the process for fabricating U-shaped trenches in silicon wafers.

This structure can then be implanted into animals or patients by directly connecting the blood vessels to flow into and out of the device, as depicted in FIG. 6. Immediate perfusion of oxygenated blood occurs, which allows survival and function of the entire living mass.

Different types of tissue, or multiple layers of the same type of tissue, can be placed adjacent to each other prior to folding and compacting, to create more complex or larger structures. For example, a tubular system can be layered onto a vascular system to fabricate glomerular tissue and collecting tubules for kidneys. Bile duct tubes can be onlaid over vascularized liver or hepatocyte tissue, to generate a bile duct drainage system. Alveolar or airway tissue can be placed on lung capillaries to make new lung tissue. Nerves or lymphatics can be added using variations of these same general techniques. The two-dimensional surface of the mold can also be varied to aid in the folding and compacting process. For example, the surface can be changed from planar to folded accordian like. It can be stacked into multiple coverging plates. It could be curvilinear or have multiple projections.

EXAMPLE 1

Micromaching of Template to Tissue Engineer Branched Vascularized Channels for Liver Fabrication.

Micromachining technologies were used on silicon and pyrex surfaces to generate complete vascular systems that may be integrated with engineered tissue before implantation. Trench patterns reminiscent of branched architecture of vascular and capillary networks were etched using standard photolithographic techniques onto silicon and pyrex surfaces to serve as templates. Hepatocytes and endothelial cells were cultured and subsequently lifted as single-cell monolayers from these two dimensional molds. Both cell types were viable and proliferative on these surfaces. In addition, hepatocytes maintained albumin production. The lifted monolayers were then folded into compact three-dimensional tissues. The goal is to lift these branched vascular networks from two dimensional templates so that they can be combined with layers of parenchymal tissue, such as hepatocytes, to form three dimensional conformations of living vascularized tissue for implantation.

Materials and Methods
Micromachining Techniques

Templates for the formation of sheets of living vascularized tissue were fabricated utilizing micromachining technology. For the present work, a single level etch was utilized to transfer a vascular network pattern into an array of connected trenches in the surface of both silicon and pyrex wafers.

In this prototype, a simple geometry was selected for patterning the vascular network. Near the edge of each wafer, a single inlet or outlet was positioned, with a width of 500 $\mu$m. After a short length, the inlet and outlet branched into three smaller channels of width 250 $\mu$m; each of these branched again into three 125 $\mu$m channels, and finally down to three 50 $\mu$m channels. Channels extend from the 50 $\mu$m channels to form a capillary network, which comprises the bulk of the layout. In between these inlet and outlet networks lies a tiled pattern of diamonds and hexagons forming a capillary bed and filling the entire space between the inlet and outlet. In one configuration, the capillary width was set at 25 $\mu$m, while in the other, capillaries were fixed at 10 $\mu$m. This geometry was selected because of its simplicity as well as its rough approximation to the size scales of the branching architecture of the liver. Layout of this network was accomplished using CADENCE software (Cadence, Chelmsford, Mass.) on a Silicon Graphics workstation. A file with the layout was generated and sent electronically to Align-Rite (Burbank, Calif.), where glass plates with electron-beam-generated patterns replicating the layout geometry were produced and returned for lithographic processing.

Starting materials for tissue engineering template fabrication were standard semiconductor grade silicon wafers (Virginia Semiconductor, Powhatan, Va.), and standard pyrex wafers (Bullen Ultrasonics, Eaton, Ohio) suitable for MEMS processing. Silicon wafers were 100 mm diameter and 525 microns thick, with primary and secondary flats cut into the wafers to signal crystal orientation. Crystal orientation was <100>, and wafers were doped with boron to a resistivity of approximately 5 W-cm. The front surface was polished to an optical finish and the back surface ground to a matte finish. Pyrex wafers were of composition identical to Corning 7740 (Corning Glass Works, Corning N.Y.), and were also 100 mm in diameter, but had a thickness of 775 microns. Both front and back surfaces were polished to an optical finish. Prior to micromachining, both wafer types were cleaned in a mixture of 1 part $H_2SO_4$ to 1 part $H_2O_2$ for 20 minutes at 140° C., rinsed 8 times in deionized water with a resistivity of 18 MW, and dried in a stream of hot $N_2$ gas.

For silicon and pyrex wafers, standard photolithography was employed as the etch mask for trench formation. Etching of pyrex wafers requires deposition of an intermediate layer for pattern transfer which is impervious to the etch chemistry. A layer of polysilicon of thickness 0.65 $\mu$m over the pyrex was utilized for this purpose. This layer was deposited using Low Pressure Chemical Vapor Deposition (LPCVD) at 570° C. and 500 mTorr via the standard silane decomposition method. In the case of silicon, photoresist alone could withstand limited exposure to two of the three etch chemistries employed. For the third chemistry, a 1.0 $\mu$m layer of silicon dioxide was thermally deposited at 1100° C. in hydrogen and oxygen.

Once the wafers were cleaned and prepared for processing, images of the prototype branching architecture were translated onto the wafer surfaces using standard MEMS lithographic techniques. A single layer of photoresist (Shipley 1822, MicroChem Corp., Newton, Mass.) was spun onto the wafer surfaces at 4000 rpm, providing a film thickness of approximately 2.4 $\mu$m. After baking at 90° C. for 30 minutes, the layer of photoresist was exposed to uv light using a Karl Suss MA6 (Suss America, Waterbury, Vt.) mask aligner. Light was passed through the lithographic plate described earlier, which was in physical contact with the coated wafer. This method replicates the pattern on the plate to an accuracy of 0.1 $\mu$m. Following exposure, wafers were developed in Shipley 319 Developer (MicroChem Corp., Newton, Mass.), and rinsed and dried in deionized water. Finally, wafers were baked at 110° C. for 30 minutes to harden the resist, and exposed to an oxygen plasma with 80 Watts of power for 42 seconds to remove traces of resist from open areas.

Silicon wafers were etched using three different chemistries, while pyrex wafers were processed using only one technique. For pyrex, the lithographic pattern applied to the polysilicon intermediate layer was transferred using a brief (approximately 1 minute) exposure to $SF_6$ in a reactive-ion-etching plasma system (Surface Technology Systems, Newport, United Kingdom). Photoresist was removed, and the pattern imprinted into the polysilicon layer was transferred into trenches in the silicon using a mixture of 2 parts $HNO_3$ to 1 part HF at room temperature. With an etch rate of 1.7 microns per minute, 20 micron deep trenches were etched into the pyrex wafers in approximately 12 minutes. Since the chemistry is isotropic, as the trenches are etched they become wider. Processing with the layout pattern with 25 $\mu$m wide capillary trenches tended to result in merging of the channels, while the use of 10 $\mu$m wide trenches avoided this phenomenon. Interferometric analysis of the channels after etching showed that surface roughness was less than 0.25 $\mu$m. Once channel etching of pyrex wafers was completed, polysilicon was removed with a mixture of 10 parts $HNO_3$ to 1 part HF at room temperature, and wafers were re-cleaned in 1 part $H_2SO_4$ to 1 part HF.

Three different chemistries were employed to etch silicon in order to investigate the interaction between channel geometry and cell behavior. First, a standard anisotropic plasma etch chemistry, using a mixture of $SF_6$ and $C4F_8$ in a switched process plasma system from STS[24], was used to produce rectangular trenches in silicon. Narrower trenches are shallower than deep trenches due to a phenomenon known as RIE lag. A second process utilized a different plasma system from STS, which produces isotropic trenches with a U-shaped profile. While the process is isotropic, widening of the trenches is not as severe as is experienced in the isotropic pyrex etching process described earlier. In both of these plasma etching cases, trenches were etched to a nominal depth of 20 $\mu$m. For the third process, anisotropic etching in KOH (45% w/w in $H_2O$ at 88° C.), the intermediate silicon dioxide layer mentioned above was employed. First, the silicon dioxide layer was patterned using HF etching at room temperature. The KOH process produces angled sidewalls rather than the rectangular profile or U-shaped profile produced by the first two recipes, respectively. Crystal planes in the <111>orientation are revealed along the angled sidewalls, due to anisotropic properties of the KOH etch process as a function of crystal orientation. Due to the self-limiting nature of the channels produced by this process, trench depth was limited to 10 $\mu$m. After completion of the silicon wafer etching, all layers of photoresist and silicon dioxide were removed, and wafers were cleaned in 1 part $H_2SO_4$:1 part $H_2O_2$ at 140° C., followed by rinsing in deionized water and drying in nitrogen gas.

For this set of experiments, no attempt was made to alter the surface chemistry of the silicon and pyrex wafers. Prior to processing, silicon wafers were uniformly hydrophobic, while pyrex wafers were equally hydrophilic, as determined by observations of liquid sheeting and sessile drop formation. After processing, unetched surfaces appeared to retain these characteristics, but the surface chemistry within the channels was not determined.

Animals

Adult male Lewis rats (Charles River Laboratories, Wilmington, Mass.), weighing 150–200 g, were used as cell donors. Animals were housed in the Animal Facility of Massachusetts General Hospital in accordance with NIH guide lines for the care of laboratory animals. They were allowed rat chow and water ad libitum and maintained in 12-hour light and dark cycle.

Cell Isolations

Male Lewis rats were used as hepatic cell donors. HCs were isolated using a modification of the two-step collagenase perfusion procedure as previously by Aiken et al., J Pediatr Surg 25, 140 (1990); Seglen PO Methods Cell Biol 13, 29 (1976). Briefly, the animals were anesthetized with Nembutal Sodium Solution (Abbott Laboratories, North Chicago, Ill.), 50 mg/kg, and the abdomen was prepared in sterile fashion. A midline abdominal incision was made and the infrahepatic inferior vena cava was cannulated with a 16-gauge angiocatheter (Becton Dickinson). The portal vein was incised to allow retrograde efflux and the suprahepatic inferior vena cava was ligated. The perfusion was performed at a flow rate of 29 ml/min initially with a calcium-free buffer solution for 5 to 6 minutes, then with a buffer containing collagenase type 2 (Worthington Biomedical Corp., Freehold, N.J.) at 37° C. The liver was excised after adequate digestion of the extracellular matrix and mechanically agitated in William's E medium (Sigma, St. Louis, Mo.) with supplements to produce a single cell suspension. The suspension was filtered through a 300 micron mesh and separated into two fractions by centrifugation at 50 g for 2 minutes at 4° C. The pellet containing the viable HC fraction was resuspended in William's E medium and further purified by an isodensity Percoll centrifugation. The resulting pellet was then resuspended in Hepatocyte Growth Medium, and cell counts and viabilities of HCs were determined using the trypan blue exclusion test.

The endothelial cells were derived from rat lung microvessels and they were purchased directly from the vendor, Vascular Endothelial Cell Technologies (Rensellaer, N.Y.).

Hepatocyte Culture Medium

William's E medium supplemented with 1 g sodium pyruvate (Sigma, St. Louis, Mo.) and 1% glutamine-penicillin-streptomycin (Gibco BRL, Gaithersburg, Md.) were used during the cell isolation process. The plating medium was Dulbecco's modified eagle medium (Gibco BRL) supplemented with 10% fetal bovine serum, 1% penicillin-streptomycin, 44 mM sodium-bicarbonate, 20 mM HEPES, 10 mM niacinamide, 30 microgram/ml L-proline, 1 mM ascorbic acid 2 phospate, 0.1 microM dexamethasone (Sigma), insulin-transferrin-sodium selenite (5 mg/L-5mg/L-5 microgram/L, Roche Molecular Biomedicals, Indianapolis, Ind.), and 20 ng/ml epidermal growth factor (Collaborative Biomedical Products, Bedford, Mass.).

Endothelial Cell Culture Medium

Dulbecco's modified eagle medium (Gibco BRL) was supplemented with 10% fetal bovine serum, 1% penicillin-streptomycin, 25 mg of ascorbic acid (Sigma), 10 mg L-alanine (Sigma), 25 mg L-proline (Sigma), 1.5 microgram cupric sulfate (Sigma), glycine (Sigma) and 1M Hepes buffer solution (Gibco BRL). The media was supplemented with 8 mg of ascorbic acid every day.

Cell attachment and lifting from non-etched silicon and pyrex wafers

Silicon and pyrex were both tested as possible substrates for the culture and lifting of endothelial cells and hepatocytes. Prior to cell seeding, the pyrex wafers were sterilized with 70% ethanol (Fisher, Pittsburg, Pa.) overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Rat lung microvascular endothelial cells was cultured on non-coated pyrex and silicon surfaces, as well as wafers coated with vitrogen (30 microgram/ml), Matrigel® (1%), or Gelatin (10 mg/ml). Once isolated, the cells were resuspended in endothelial cell culture medium, seeded uniformly onto the wafer at a density of $26.7 \times 10^3$ cells/cm$^2$, and cultured at 5% $CO_2$ and 37° C. After reaching confluence, the ability of the monolayer of endothelial cells to lift from the wafers was tested using a cell scrapper to promote detachment.

The rat hepatocytes were also cultured on non-coated pyrex and silicon, as well as wafers coated with a thin and thick layers of vitrogen (30 microgram/ml and 3 microgram /ml) and Matrigel (1%) in order to determine the optimal methods for lifting hepatocyte sheets. Once isolated, the hepatocytes were resuspended in hepatocyte growth media, seeded onto the wafer at a density of $111.3 \times 10^3$ cells/cm$^2$, and cultured at 5% $CO_2$ and 37° C. Cell attachment and growth was observed daily using microscopy and cell lifting occurred spontaneously.

After determining which method for culturing was best for lifting the hepatocytes and endothelial cells in an intact layer, both membranes were fixed in 10% buffered formalin for 1 hr and harvested for histological study, and the hepatocytes were stained immunohistochemically.

Immunohistochemical Staining

The hepatocyte cell monolayer membrane was fixed in 10% buffered formalin and processed for hematoxylin-eosin and immunohistochemical staining using a labeled streptavidin biotin method (LSAB2 kit for rat specimen, DAKO, Carpinteria, Calif.). The primary antibody was rabbit anti-albumin (ICN, Costa Mesa, Calif.). Three-micron sections were prepared and deparafinized. The specimens were treated with peroxidase blocking buffer (DAKO) to prevent the nonspecific staining. Sections were stained with albumin diluted with phosphate buffered saline, followed by biotinylated anti-rabbit antibody and HRP conjugated streptavidin. Sections were treated with DAB as substrate and were counterstained with hematoxylin.

Albumin Production

To assess hepatocyte function, albumin concentration in the culture medium was measured every 24 hours for 5 days pre-cell detachment using an enzyme linked immunosorbent assay (n=5), as described by Schwereet al., *Clinica Chemica Acta* 163, 237 (1987). In brief, a 96 well microplate was coated with anti-rat albumin antibody (ICN). After blocking non-specific responses with a 1% gelatin solution, each sample was seeded onto the plate and incubated for 1 hour. This was followed by another 1 hour incubation with peroxidase conjugated anti-rat albumin antibody (ICN). Finally, the substrate was added and extinction was measured with a microplate reader at 410 nm. $R^2$ of the standard curve was >0.99.

Statistical Analysis

All data was expressed as mean ±SD. Statistical analysis was performed with a paired t-test. Statistical significance was determined as when the p value of each test was less than 0.05.

Cell Attachment to Etched Silicon and Pyrex Wafers

Endothelial cells and hepatocytes were also seeded onto etched silicon and pyrex wafers. Prior to cell seeding, the pyrex wafers were sterilized with 70% ethanol (Fisher) overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Onto these wafers were seeded rat lung microvascular endothelial cells at a density of $26.7 \times 10^3$ cells/cm$^2$, or rat hepatocytes at a density of $111.3 \times 103$ cells/cm$^2$. These cells were cultured at 5% $CO_2$ and 37° C., and their attachment and growth observed daily using microscopy.

Implantation of Hepatocyte Sheets into the Rat Omentum

Hepatocytes were cultured on silicon wafers coated with a thin layer of vitrogen (30 microgram/ml), and lifted in sheets. Retrorsine is a drug known to inhibit the regeneration of the normal liver by producing a block in the hepatocyte cell cycle with an accumulation of cells in late S and/or $G_2$ phase (Peterson J E J *Pathol Bacteriol* 89, 153 (1965)). This drug was administered into the peritoneal cavity of two rats at a dose of 3 mg/ml/100 g on day 0, and after two weeks. Three weeks later, a portacaval shunt was created, and the following week a hepatocyte sheet, lifted after four days culture on vitrogen coated silicon (30 microgram/ml), was implanted onto the microvasculature of the rat omentum and rolled into a three-dimensional cylinder, and a 60% hepatectomy was performed. The rolled omentum with hepatocytes was harvested at four weeks and at three months after implantation and analyzed using histology.

Results

Micromachining

Figure 9A:
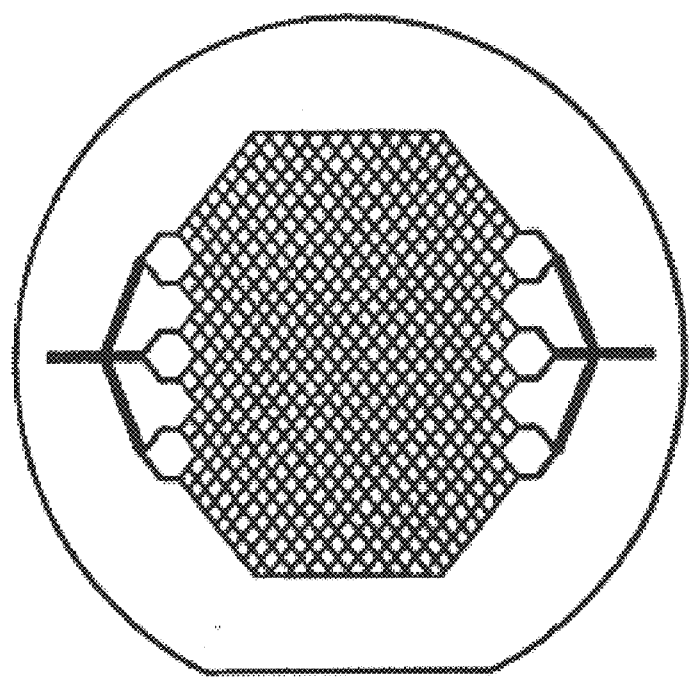
FIG. 9a shows the vascular branching network pattern used for silicon and pyrex wafer micromachining (FIG. 9a)
Figure 9B:
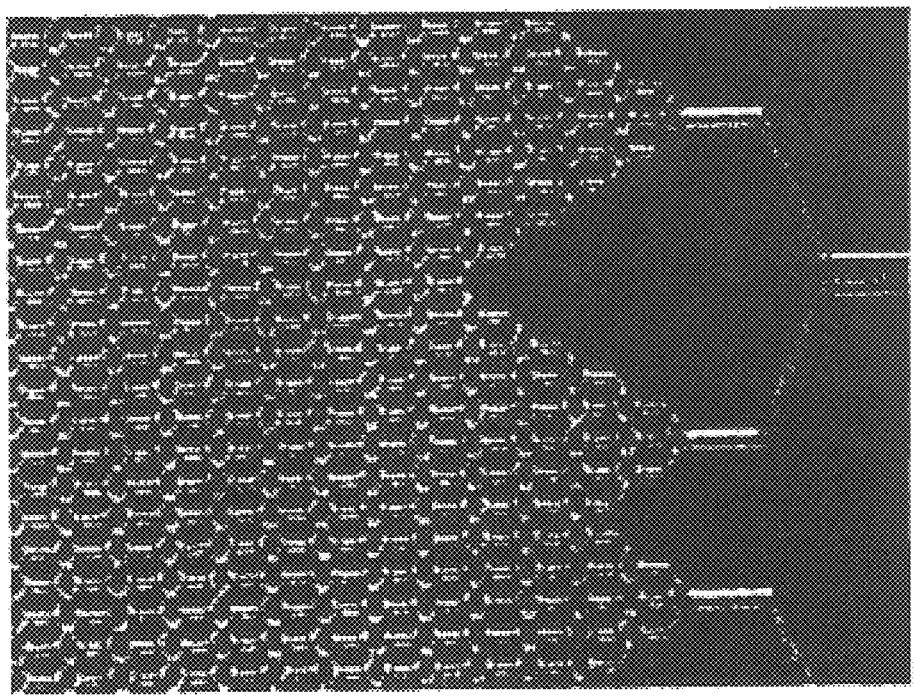
FIG. 9b shows the optical micrograph or portion of the capillary network etched into the silicon wafer using the process shown in FIG. 7.
Figure 9C:
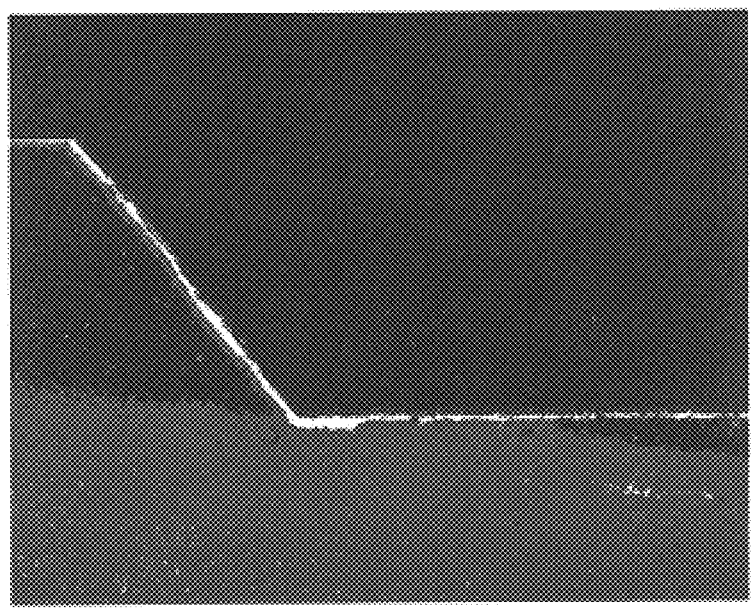
FIG. 9c is a scanning electron micrograph of the anisotrophic etching process used to form angled sidewall trenches.

A schematic of the vascular branching network design used as a template for micromachining is shown in FIG. 9a. This pattern was transferred to silicon and pyrex wafers using the processes described in the Materials and Methods section. Typical trench depths of 20 microns on silicon and 10 microns on glass were achieved utilizing these processes. An optical micrograph of a portion of the capillary network etched into a silicon wafer is shown in FIG. 9b. In FIG. 9c, a Scanning Electron Micrograph cross-section of an angled trench etched using the anisotropic etching process described earlier is shown. This process resulted in excellent adhesion and enhanced lifting of living tissue.

Growth and Lifting of Cells from the Silicon and Pyrex Wafers

The adhesion and growth of endothelial cells and hepatocytes on several different substrate surfaces was compared. On all pyrex wafers, coated or noncoated, the endothelial cells proliferated and grew to confluence within four days. These cells did not lift spontaneously, and when scraped, did not lift as a single sheet. In addition, when the non-coated silicon wafers were seeded with endothelial cells, the cell sheet fragmented upon lifting. On the other hand, endothelial cells seeded onto silicon surfaces coated with vitrogen (30 microgram/ml), Matrigel (1%), and gelatin (10 mg/ml) did lift with the use of mechanical means (i.e. a cell scraper), and provided an intact monolayer sheet of endothelial cells. Upon observation, there were no significant differences in the effects of the three coatings on the detached cell sheets.

Hepatocytes also attached and spread well on all coated and non-coated pyrex wafers, and did not lift spontaneously or in sheets when scraped after several days of growth. However, when seeded onto silicon wafers, they lifted spontaneously on all the non-coated and coated wafers. The hepatocyte sheets lifted from the non-coated wafers after 3 days, but were very fragile and fragmented easily. The monolayers that lifted from the thin and thickly coated vitrogen substrates (30 microgram/ml and 3 microgram/ml) lifted after 4 days in culture to form an intact hepatocyte layer. Cells lifted from the Matrigel (1%) coated silicon wafers after 5 days in culture. There were no significant differences in appearance between the cell sheets lifted from the vitrogen and Matrigel coated wafers.

Histological assessment of the detached cell monolayers of both hepatocytes and endothelial cells manifested promising results. Hemotoxylin and Eosin (H&E) staining of both showed that all cells were viable and that most were undergoing mitoses. The endothelial cells were observed to be primarily attenuated and to form a single-celled alignment. The monolayer of hepatocytes showed each cell to be of a spheriod configuration with eosinophilic floculent cytoplasm and a large nucleus with a bright red nucleolus, similar to that seen in the native liver. Moreover, cellular attachments were less attenuated than the endothelial cells. Thus, these results are reminiscent of each of the cell types' specific functions. In biological systems, the endothelium functions to provide a thin, smooth outer surface of a barrier and a transport channel and so it is understandable that these cells are observed here to be primarily attenuated and in a single-celled array. The hepatocytes have more of a tendency to form tissue and so less of a single-celled array and more of a rounded multi-layered array is seen.

Albumin secretion into the hepatocyte culture medium at day 2, 3, 4, and 5 was 165.96±29.87, 164.44±17.22, 154.33±18.46, 115.47±18.09 (microgram/day, Graph 1), respectively. Though there was a statistically significant difference between day 4 and day 5, no significant differences were observed between day 2, day 3, and day 4 ($p<0.05$ by the paired t-test). Hence, this data shows that cells cultured on silicon wafers were able to maintain a fairly constant albumin production rate until day 4.

Moreover, through immunohistochemical staining of the detached hepatocyte monolayers, many cells were stained positive for albumin indicating further that hepatocyte function was maintained on silicon wafers.

Implantation of Hepatocyte Sheet into the Rat Omentum

H&E staining of hepatocyte sheets implanted into rat omentum demonstrated that all cells were viable and showed proliferation at four weeks and three months. The implanted hepatocyte monolayer sheets, when harvested, were over 5 cell layers thick in most areas. This study demonstrates that silicon microfabrication technology can be utilized to form large sheets of living tissue. It also demonstrates the feasibility of etching ordered branching arrays of channels that allow living endothelial cells to line the luminal surface of the channels. In addition, it has been shown that organized sheets of engineered hepatocyte tissue and endothelial tissue can be lifted from the surface of silicon or pyrex wafers and can be folded into a compact three dimensional configuration. The hepatocyte sheets have then been placed into rats on the highly vascular surface of the omentum. That structure has then been rolled into a three dimensional cylinder as a model for an engineered vasculature. Vascularized hepatic tissue was formed as a permanent graft.

Modifications and variations of the method and devices described herein will be obvious to those skilled in the art and are intended to be encompassed by the following claims.

I claim:

1. A laminated structure consisting essentially of multiple layers, wherein each layer consists essentially of tissue and vasculature, wherein the layers are assembled adjacent to each other by folding and compacting, the resulting vasculature is in three dimensions throughout the structure, and the structure has connections for flow into and out of the vasculature, and whereby the structure can be implanted directly by connecting blood vessels to flow into and out of the vasculature.

2. The structure of claim 1 wherein the vasculature comprises endothelial cells.

3. The structure of claim 2 further comprising cells selected from the group consisting of parenchymal cells, cells forming cartilage or bone, muscle cells, and nerve cells.

4. The structure of claim 3 wherein the parenchymal cells are derived from organs selected from the group consisting of heart, liver, pancreas, intestine, brain, kidney, reproductive tissues and lung.

5. The structure of claim 1 comprising glomerular tissue and a bile duct drainage system.

6. The structure of claim 1 comprising alveolar or airway tissue.

7. The structure of claim 1 comprising nerves or lymphatics.

* * * * *